(12) United States Patent
Slack

(10) Patent No.: US 8,124,360 B2
(45) Date of Patent: Feb. 28, 2012

(54) USE OF A T1R2 NUCLEIC ACID SEQUENCE TO IDENTIFY TASTANTS

(75) Inventor: Jay Patrick Slack, Loveland, OH (US)

(73) Assignee: Givaudan S.A. (CH)

( * ) Notice: Subject to any disclaimer, the term of this patent is extended or adjusted under 35 U.S.C. 154(b) by 32 days.

(21) Appl. No.: 12/297,695

(22) PCT Filed: Apr. 19, 2007

(86) PCT No.: PCT/CH2007/000185
§ 371 (c)(1),
(2), (4) Date: Nov. 3, 2008

(87) PCT Pub. No.: WO2007/121599
PCT Pub. Date: Nov. 1, 2007

(65) Prior Publication Data
US 2009/0176266 A1    Jul. 9, 2009

Related U.S. Application Data

(60) Provisional application No. 60/793,686, filed on Apr. 20, 2006.

(51) Int. Cl.
*C07K 14/705* (2006.01)
*G01N 33/567* (2006.01)
(52) U.S. Cl. .................... 435/7.21; 435/7.1; 435/7.2
(58) Field of Classification Search .................. None
See application file for complete search history.

(56) References Cited

U.S. PATENT DOCUMENTS

| | | | |
|---|---|---|---|
| 4,115,538 A | 9/1978 | Satoh et al. | |
| 5,436,128 A | 7/1995 | Harpold et al. | |
| 5,919,649 A | 7/1999 | Habener et al. | |
| 6,955,887 B2 * | 10/2005 | Adler et al. | 435/7.2 |
| 2004/0214239 A1 | 10/2004 | Servant | |
| 2005/0032158 A1 | 2/2005 | Adler et al. | |

FOREIGN PATENT DOCUMENTS

| | | |
|---|---|---|
| WO | WO 92/01810 | 2/1992 |
| WO | WO 01 18050 | 3/2001 |
| WO | WO 2004/055048 A | 7/2004 |
| WO | WO2005/015158 | 2/2005 |

OTHER PUBLICATIONS

Ishimaru Yoshiro et al: "Two families of candidate taste receptors in fishes" Mechanisms of Development, vol. 122, No. 12, Dec. 2005, pp. 1310-1321.
Broach, J.R. and J. Thorner "High-throughput screening for drug discovery", (1996) Nature 384 (supp.): 14-16).
Knight and Grigliatti, "Chimeric G Proteins Extend the Range of Insect Cell-Based Functional Assays for Human G Protein-Coupled Receptors" (2004) Journal of Receptors and Signal Transduction 24: 241-256.
Kenimer & Nirenberg, "Desensitization of Adenylate Cyclase to Prostaglandin $E^1$ or 2-Chloroadenosine" 1981, Mol. Pharmacol. 20: 585-591.
Traynor and Nahorski, "Modulation by μ-Opioid Agonists of Guanosine-5'-O-(3-[$^{35}$S]thio)triphosphate Binding to Membranes from Human Neuroblastoma SH-SY5Y Cells" 1995, Mol. Pharmacol. 47: 848-854.
Hafner, "Cytosensor Microphysiometer: technology and recent applications", 2000, Biosens. Bioelectron. 15: 149-158.
Gijon et al., "Cytosolic Phospholipase $A_2$ is Required for Macrophage Arachidonic Acid Release by Agonists That Do and Do Not Mobilize Calcium" 2000, J.Biol. Chem., 275:20146-20156.
Horton & Baxendale, "Mass Measurements of Cyclic AMP Formation by Radioimmunoassay, Enzyme Immunoassay, and Scintillation Proximity Assay" 1995, Methods Mol. Biol. 41: Chap. 8, 91-105.
Felley-Bosco et al., "Constitutive Expression of Inducible Nitric Oxide Synthase in Human Bronchial Epithelial Cells Induces c-*fos* and Stimulates the cGMP Pathway" Am. J. Resp. Cell and mol. Biol., (1994) 11:159-164.
Kikkawa et al., 1982, "Calcium-activated, Phospholipid-dependent Protein Kinase from Rat Brain"; Journal of Biological Chemistry; 257: 13341.
Pinna & Ruzzene, "How do protein kinases recognize their substrates?" 1996, Biochem. Biophys. Acta 1314: 191-225.
Li et al. "Human receptors for sweet and umami taste" 2002, Proc Natl Acad Sci USA 99(7), 4692-6.

* cited by examiner

*Primary Examiner* — John Ulm
(74) *Attorney, Agent, or Firm* — Curatolo Sidoti Co., LPA; Joseph G. Curatolo; Salvatore A. Sidoti

(57) ABSTRACT

Provided are functional methods using the T1R2 monomer of the T1R2/T1R3 sweet receptor to identify agonists and modulators of the sweet taste response.

20 Claims, No Drawings

SEQUENCE LISTING

```
<160> NUMBER OF SEQ ID NOS: 2

<210> SEQ ID NO 1
<211> LENGTH: 2520
<212> TYPE: DNA
<213> ORGANISM: human

<400> SEQUENCE: 1
atggggccca gggcaaagac catctcctcc ctgttcttcc tcctatgggt cctggctgag      60
ccggctgaga actcggactt ctacctgcct ggggattacc tcctgggtgg cctcttctcc     120
ctccatgcca acatgaaggg cattgttcac cttaacttcc tgcaggtgcc catgtgcaag     180
gagtatgaag tgaaggtgat aggctacaac ctcatgcagg ccatgcgctt tgcggtggag     240
gagatcaaca atgacagcag cctgctgcct ggtgtgctgc tgggctatga gatcgtggat     300
gtgtgctaca tctccaacaa tgtccagccg gtgctctact tcctggcaca cgaggacaac     360
ctccttccca tccaagagga ctacagtaac tacatttccc gtgtggtggc tgtcattggc     420
cctgacaact ccgagtctgt catgactgtg gccaacttcc tctccctatt tctccttcca     480
cagatcacct acagcgccat cagcgatgag ctgcgagaca aggtgcgctt cccggctttg     540
ctgcgtacca cacccagcgc cgaccaccac atcgaggcca tggtgcagct gatgctgcac     600
ttccgctgga actggatcat tgtgctggtg agcagcgaca cctatggccg cgacaatggc     660
cagctgcttg gcgagcgcgt ggcccggcgc gacatctgca tcgccttcca ggagacgctg     720
cccacactgc agcccaacca gaacatgacg tcagaggagc gccagcgcct ggtgaccatt     780
gtggacaagc tgcagcagag cacagcgcgc gtcgtggtcg tgttctcgcc cgacctgacc     840
ctgtaccact tcttcaatga ggtgctgcgc cagaacttca ctggcgccgt gtggatcgcc     900
tccgagtcct gggccatcga cccggtcctg cacaacctca ggagctgcg ccacttgggc     960 accttcctgg catcaccat ccagagcgtg cccatcccgg gcttcagtga gttccgcgag    1020
tggggcccac aggctgggcc gccacccctc agcaggacca gccagagcta tcctgcaac    1080
```

-continued

```
caggagtgcg acaactgcct gaacgccacc ttgtccttca acaccattct caggctctct    1140
ggggagcgtg tcgtctacag cgtgtactct gcggtctatg ctgtggccca tgccctgcac    1200
agcctcctcg gctgtgacaa aagcacctgc accaagaggg tggtctaccc ctggcagctg    1260
cttgaggaga tctggaaggt caacttcact ctcctggacc accaaatctt cttcgacccg    1320
caaggggacg tggctctgca cttggagatt gtccagtggc aatgggaccg agccagaat     1380
cccttccaga gcgtcgcctc ctactacccc ctgcagcgac agctgaagaa catccaagac    1440
atctcctggc acaccatcaa caacacgatc cctatgtcca tgtgttccaa gaggtgccag    1500
tcagggcaaa agaagaagcc tgtgggcatc acgtctgct gcttcgagtg catcgactgc     1560
cttcccggca ccttcctcaa ccacactgaa gatgaatatg aatgccaggc ctgcccgaat    1620
aacgagtggt cctaccagag tgagacctcc tgcttcaagc ggcagctggt cttcctggaa    1680
tggcatgagg cacccaccat cgctgtggcc ctgctggccg ccctgggctt cctcagcacc    1740
ctggccatcc tggtgatatt ctggaggcac ttccagacac ccatagttcg ctcggctggg    1800
ggccccatgt gcttcctgat gctgacactg ctgctggtgg catacatggt ggtcccggtg    1860
tacgtggggc cgcccaaggt ctccacctgc ctctgccgcc aggccctctt tcccctctgc    1920
ttcacaatct gcatctcctg tatcgccgtg cgttctttcc agatcgtctg cgccttcaag    1980
atggccagcc gcttcccacg cgcctacagc tactgggtcc gctaccaggg gcctacgtc     2040
tctatggcat ttatcacggt actcaaaatg gtcattgtgg taattggcat gctggccacg    2100
ggcctcagtc ccaccacccg tactgacccc gatgaccccc agatcacaat tgtctcctgt    2160
aaccccaact accgcaacag cctgctgttc aacaccagcc tggacctgct gctctcagtg    2220
gtgggtttca gcttcgccta catgggcaaa gagctgccca ccaactacaa cgaggccaag    2280
ttcatcaccc tcagcatgac cttctatttc acctcatctg tctccctctg caccttcatg    2340
tctgcctaca gcggggtgct ggtcaccatc gtggacctct tggtcactgt gctcaacctc    2400
ctggccatca gcctgggcta cttcggcccc aagtgctaca tgatcctctt ctacccggag    2460
cgcaacacgc ccgcctactt caacagcatg atccagggct acaccatgag gagggactag    2520
```

<210> SEQ ID NO 2
<211> LENGTH: 839
<212> TYPE: PRT
<213> ORGANISM: human

<400> SEQUENCE: 2

```
Met Gly Pro Arg Ala Lys Thr Ile Ser Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125
```

-continued

```
Ser Asn Tyr Ile Ser Arg Val Val Ala Val Ile Gly Pro Asp Asn Ser
        130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Ile Glu
                180                 185                 190

Ala Met Val Gln Leu Met Leu His Phe Arg Trp Asn Trp Ile Ile Val
            195                 200                 205

Leu Val Ser Ser Asp Thr Tyr Gly Arg Asp Asn Gly Gln Leu Leu Gly
210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
                260                 265                 270

Val Val Phe Ser Pro Asp Leu Thr Leu Tyr His Phe Phe Asn Glu Val
            275                 280                 285

Leu Arg Gln Asn Phe Thr Gly Ala Val Trp Ile Ala Ser Glu Ser Trp
290                 295                 300

Ala Ile Asp Pro Val Leu His Asn Leu Thr Glu Leu Arg His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
                340                 345                 350

Thr Ser Gln Ser Tyr Thr Cys Asn Gln Glu Cys Asp Asn Cys Leu Asn
            355                 360                 365

Ala Thr Leu Ser Phe Asn Thr Ile Leu Arg Leu Ser Gly Glu Arg Val
370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
                420                 425                 430

Asp His Gln Ile Phe Phe Asp Pro Gln Gly Asp Val Ala Leu His Leu
    435                 440                 445

Glu Ile Val Gln Trp Gln Trp Asp Arg Ser Gln Asn Pro Phe Gln Ser
450                 455                 460

Val Ala Ser Tyr Tyr Pro Leu Gln Arg Gln Leu Lys Asn Ile Gln Asp
465                 470                 475                 480

Ile Ser Trp His Thr Ile Asn Asn Thr Ile Pro Met Ser Met Cys Ser
                485                 490                 495

Lys Arg Cys Gln Ser Gly Gln Lys Lys Lys Pro Val Gly Ile His Val
                500                 505                 510

Cys Cys Phe Glu Cys Ile Asp Cys Leu Pro Gly Thr Phe Leu Asn His
            515                 520                 525

Thr Glu Asp Glu Tyr Glu Cys Gln Ala Cys Pro Asn Asn Glu Trp Ser
530                 535                 540

Tyr Gln Ser Glu Thr Ser Cys Phe Lys Arg Gln Leu Val Phe Leu Glu
545                 550                 555                 560
```

```
Trp His Glu Ala Pro Thr Ile Ala Val Ala Leu Leu Ala Ala Leu Gly
                565                 570                 575
Phe Leu Ser Thr Leu Ala Ile Leu Val Ile Phe Trp Arg His Phe Gln
                580                 585                 590
Thr Pro Ile Val Arg Ser Ala Gly Gly Pro Met Cys Phe Leu Met Leu
                595                 600                 605
Thr Leu Leu Leu Val Ala Tyr Met Val Val Pro Val Tyr Val Gly Pro
                610                 615                 620
Pro Lys Val Ser Thr Cys Leu Cys Arg Gln Ala Leu Phe Pro Leu Cys
625                 630                 635                 640
Phe Thr Ile Cys Ile Ser Cys Ile Ala Val Arg Ser Phe Gln Ile Val
                645                 650                 655
Cys Ala Phe Lys Met Ala Ser Arg Phe Pro Arg Ala Tyr Ser Tyr Trp
                660                 665                 670
Val Arg Tyr Gln Gly Pro Tyr Val Ser Met Ala Phe Ile Thr Val Leu
                675                 680                 685
Lys Met Val Ile Val Val Ile Gly Met Leu Ala Thr Gly Leu Ser Pro
                690                 695                 700
Thr Thr Arg Thr Asp Pro Asp Asp Pro Lys Ile Thr Ile Val Ser Cys
705                 710                 715                 720
Asn Pro Asn Tyr Arg Asn Ser Leu Leu Phe Asn Thr Ser Leu Asp Leu
                725                 730                 735
Leu Leu Ser Val Val Gly Phe Ser Phe Ala Tyr Met Gly Lys Glu Leu
                740                 745                 750
Pro Thr Asn Tyr Asn Glu Ala Lys Phe Ile Thr Leu Ser Met Thr Phe
                755                 760                 765
Tyr Phe Thr Ser Ser Val Ser Leu Cys Thr Phe Met Ser Ala Tyr Ser
                770                 775                 780
Gly Val Leu Val Thr Ile Val Asp Leu Leu Val Thr Val Leu Asn Leu
785                 790                 795                 800
Leu Ala Ile Ser Leu Gly Tyr Phe Gly Pro Lys Cys Tyr Met Ile Leu
                805                 810                 815
Phe Tyr Pro Glu Arg Asn Thr Pro Ala Tyr Phe Asn Ser Met Ile Gln
                820                 825                 830
Gly Tyr Thr Met Arg Arg Asp
                835
```

USE OF A T1R2 NUCLEIC ACID SEQUENCE TO IDENTIFY TASTANTS

CROSS REFERENCE TO RELATED APPLICATIONS

This application is a national stage application of International Application No. PCT/CH2007/000185, filed 19 Apr. 2007, which claims the benefit of U.S. Provisional Patent Application No. 60/793,686, filed 20 Apr. 2006 from which applications priority is claimed, and which are incorporated herein by reference.

The invention relates to methods based on the T1R2 receptor protein, which is used to identify sweet taste modulators including sweet tastants in functional assay methods. Assays with T1R2 may be used to identify agents that can modulate the taste response in humans (sweet taste modulators), and thereby render certain foods more palatable or increase patient compliance in oral pharmaceutics and nutraceutics. Such sweet taste modulators include sweet tastants that elicit a taste response in humans.

The detection of sweet taste is known to be mediated by a receptor comprised of two subunits, T1R2 and T1R3, which are specifically expressed in taste receptor cells, and form a dimeric sweet taste receptor complex (T1R2/T1R3 heterodimer). Both subunits belong to the family of so-called "G-protein coupled receptors" or GPCRs, in particular class-C GPCRs.

Like most other GPCRs, the class-C receptors have a heptahelical transmembrane domain (TMD). However, unlike other types of GPCRs, the class-C GPCRs also have a large extracellular domain composed of two parts: a "venus flytrap module" (VFTM) that is involved in ligand binding; and a cysteine-rich domain (CRD), that contains nine highly conserved cysteines and that links the VFTM to the TMD. A variable length intracellular C-terminal tail completes the class-C receptor.

Activation of the sweet receptor response was thought to require both subunits of the dimeric sweet receptor complex, and to date, all sweeteners tested activate the T1R2/T1R3 heterodimer. Published tests conducted with the separate subunits of the human sweet receptor (T1R2 homomer or T1R3 homomer) have shown no activity, while the T1R2/T1R3 heterodimer responds to a broad spectrum of chemically diverse sweeteners, ranging from natural sugars (sucrose, fructose, glucose, maltose), sweet amino acids (D-tryptophan), and artificial sweeteners (acesulfame-K, aspartame, cyclamate, saccharin, sucralose), to sweet tasting proteins (monellin, thaumatin, brazzein) (compare for example Li et al. (2002), Proc Natl Acad Sci USA 99(7), 4692-6). Studies of chimeric T1R receptors and site-directed mutagenesis indicate that the sweet compound cyclamate binds in the TMD of T1R3, thereby activating the heterodimeric T1R2/T1R3 receptor complex. Conversely, brazzein, a sweet protein, is reported to bind in the cysteine-rich domain of T1R3, thus activating the heterodimeric T1R2/T1R3 receptor complex.

T1R2 homomer binding assays are described in US 20050032158. Binding assays show binding only, as opposed to functional receptor activation, and are end-point-based and time consuming compared to faster functional assay that involve kinetic measurements. US 20050032158 further describes functional assays including cell-based assays for T1Rs, which are suitable for the known functional receptors T1R1/T1R3 and T1R2/T1R3.

To date, not only has there been no showing that one of the TAS1R monomers can not only bind sweet compounds, but also activate G-proteins in the absence of the other obligate monomeric partner, but the presence of both subunits (i.e. the T1R2/T1R3 heterodimer receptor complex for sweet), was believed to be essential for signal transduction.

Applicant found that the known T1R2 homomer forms, surprisingly, a functional sweet receptor that not only binds a sweet tastant (for example perillartine, which is a synthetic oxime approximately 370-times more potent/sweet than sucrose), but is also able to elicit a functional response and activate G-Proteins in the absence of T1R3.

The terms T1R2 "homomer" or "homomeric" polypeptide, protein, or receptor as used herein are meant to encompass the monomer, dimmer or oligomer of the T1R2 polypeptide or protein, as opposed to the heterodimeric T1R2.T1R3 receptor complex.

In methods according to the invention, cells expressing both T1R2 and a G-protein but not T1R3, are contacted with test agents, optionally in combination with known or newly determined sweet tastants, to determine the properties of said agents as sweet taste modulators. The assays may therefore be used to identify a tested agent as sweet tastant or modulator of the sweet response (of the sweet tastant, T1R2, or downstream events).

The functional effects of the agent on the receptor and G-protein are determined by a suitable functional assay, without limitation, for example an assay that measures changes in parameters of the transduction pathways such as intracellular IP3 and $Ca^{2+}$, or by other G-protein specific assays such as labeling with GTPγS, according to techniques known in the art.

In practising the various aspects and embodiments of the method in relation to cloning, elucidating ligand-receptor pairs, and finding modulators of the sweet response, recourse is made to conventional techniques in molecular biology, microbiology and recombinant technology. These include the various known methods suitable for G-protein coupled receptors (GPCRs) including T1R2. Accordingly, the skilled person is fully apprised of such techniques and as such they are hereafter treated only summarily in order to more fully describe the context of the methods.

SUMMARY

In a first aspect, provided is a method to identify an agent that modulates sweet taste signaling in taste cells, the method comprising: (i) contacting the cells that express a T1R2 homomeric sweet receptor that responds to sweet taste stimuli with an agent, optionally in presence of another agent; and (ii) determining whether at least one agent affects the functional activity of said T1R2 sweet receptor in said cells by at least one functional response in said cells;
wherein said T1R2 sweet receptor is selected from the group consisting of a polypeptide substantially homologous to SEQ ID NO:2, a polypeptide encoded by a nucleotide substantially homologous to SEQ ID NO:1 as determined by sequence identity, and a polypeptide encoded by a nucleotide substantially homologous to SEQ ID NO:1 as determined by hybridisation;
wherein the substantially homologous polypeptide has a sequence identity of at least 69%;
wherein the substantially homologous nucleotide as determined by sequence identity has a sequence identity of at least 64%;
wherein the substantially homologous nucleotide as determined by hybridisation hybridises under stringent hybridization conditions at a temperature of 42° C. in a solution consisting of 50% formamide, 5×SSC, and 1% SDS, and washing at 65° C. in a solution consisting of 0.2×SSC and 0.1% SDS;

and wherein the T1R2 homomeric sweet receptor expressing cells do not express a T1R3 receptor.

In one embodiment, said method is a method wherein the cells also express a G-protein. The functional response in the G-protein expressing cells can, for example, be determined by measuring a change in an intracellular messenger such as IP3 and calcium$^{2+}$.

In another embodiment, said method is a method wherein the G-Protein is a chimeric G-protein based on Gaq-Gustducin.

In yet another embodiment, said method is a method wherein the G-Protein is the chimeric G-protein G alpha 16-gustducin 44.

In still another embodiment, said method is a method wherein step (ii) is performed by measuring a change in or caused by intracellular messengers.

In another embodiment, the above methods are methods wherein the cells are selected from the group consisting of bacterial cells, eucaryotic cells, yeast cells, insect cells, mammalian cells, amphibian cells, and worm cells.

In certain embodiments, the cell is a mammalian cell, for example, a cell selected from the group consisting of CHO, COS, HeLa and HEK-293 cells.

In another embodiment, the above methods are methods wherein step (i) further comprises contacting the T1R2 sweet receptor with a test agent in presence of a sweet tastant. The sweet tastant may be, for example, perillartine.

In another aspect, a kit is provided, the kit comprising:
(i) recombinant cells that express a T1R2 receptor homomer, or a substantially similar homologue thereof, but that do not express a T1R3 receptor, and
(ii) an agonist of the T1R2 homomer,
for combined use to identify test agents as modulators of the T1R2 homomer.

In yet another aspect the invention is directed to a method of using the above-described kit, wherein the following successive steps are performed:
(i) The recombinant cells are grown on the solid support, and
(ii) test agents at concentrations from about 1 nM to 100 mM or more are added to the culture medium of defined plates or wells in the presence of the agonist in a suitable concentration,
(iii) a change in a functional response of the cells is determined by comparing the response in presence and absence of the test agent, and the test agent is thereby identified as a modulator of the T1R2 homomer or a substantially similar homologue thereof.

DETAILED DESCRIPTION

Cells Used in Assays

Useful cells in screens or assays according to the invention are cells that contain no T1R3. Transfected or endogenous T1R3 can negatively interfere with methods that determine agonist responses of T1R2 or the change of said responses dependent on another modulator. The absence of T1R3 provides a null background for the determination of T1R2 activation, so that observed signals can be directly attributed to T1R2 activity. This allows the identification of agents that specifically modulate T1R2, and excludes agents that activate T1R3, which could also include umami tastants, as T1R3 is part of both the sweet and the umami heterodimers.

Suitable eucaryotic cells include eucaryotic cells that do not contain T1R3, for example, without limitation, mammalian cells, yeast cells, or insect cells (including Sf9), amphibian cells (including melanophore cells), or worm cells including cells of *Caenorhabditis* (including *Caenorhabditis elegans*).

Suitable mammalian cells that do not contain T1R3, include, for example, COS cells (including Cos-1 and Cos-7), CHO cells, HEK293 cells, HEK293T cells, HEK293 T-Rex™ cells, or other transfectable eucaryotic cell lines.

Suitable bacterial cells that do not contain T1R3 include *E. coli*.

Cells are transfected with a GPCR and a G-Protein (which links the receptor to a phospholipase C signal transduction pathway) transiently or stably, as is well known in the art. An excellent heterologous expression system that employs the chimeric G-protein G alpha 16-gustducin 44 (also known as G.sub..alpha.16 gust(ducin)44, G.sub.alpha.16gust(ducin)44, Gα16gust(ducin)44, Ga16gust(ducin)44, $G_{\alpha 16\text{-}gustducin\ 44}$, or as used herein-below, "G16gust44") which provides for enhanced coupling to taste GPCRs, is described in detail in WO 2004/055048. Alternatively, other chimeric G-proteins based on Gaq-Gustducin described in WO 2004/055048, or other G-Proteins, for example, G16 or G15, may also be used.

T1R2 can be expressed in a cell with a G-protein that links the receptor to a signal transduction pathway, for example, the phospholipase C signal transduction pathway, or signal transduction pathways including, for example, the following: adenylate cyclase, guanylate cyclase, phospholipase C, IP3, GTPase/GTP binding, arachinoid acid, cAMP/cGMP, DAG, protein kinase c (PKC), MAP kinase tyrosine kinase, or ERK kinase.

Alternatively, any suitable reporter gene may be linked to a T1R2-activation responsive promoter and used to determine T1R2 activity, as described in more detail herein-below.

Vector Constructs Used in Cells Described Herein-Above:

The vector constructs for expressing the GPCR and/or the G-Protein in such cells may be produced in a manner known per se using Polymerase Chain Reactions. After verification of the sequence, cDNA fragments may be sub-cloned into a suitable vector, for example pcDNA 3.1 mammalian expression vector for mammalian cells, and transiently transfected in a mammalian host cell to enable the correct expression of the gene.

After a post-transfection period, for example 48 hours, cell lysates may be prepared, analysed by a Western-Blot analysis in order to confirm the correct expression of the protein. Once correct protein expression is confirmed, suitable cells, for example mammalian cells including HEK293T cells and HEK T-Rex™, may be transfected to generate cells stably expressing the protein according to techniques well known in the art.

Alternatively, a variety of non-mammalian expression vector/host systems can be used to contain and express sequences encoding the T1R2 GPCR. These include, for example, microorganisms including bacteria transformed with recombinant bacteriophage, plasmid, or cosmid DNA expression vectors; yeast transformed with yeast expression vectors; insect cell systems infected with viral expression vectors (for example baculovirus), or with bacterial expression vectors (for example pBR322 plasmids).

Examples of specific vectors that may be used with the systems described herein-above are described in "G-protein coupled receptors (Signal Transduction Series)"; Editors: Tatsuya Haga and Gabriel Berstein, 1st ed., CRC Press—Boca Raton Fla.; September 1999.

In bacterial systems, a number of cloning and expression vectors may be selected depending upon the use intended for polynucleotide sequences encoding the GPCR. For example, routine cloning, subcloning, and propagation of polynucleotide sequences encoding a GPCR can be achieved using a multifunctional *E. coli* vector such as PBLUESCRIPT (Stratagene, La Jolla Calif.) or PSPORT1 plasmid (Life Technologies). Ligation of sequences encoding a GPCR into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. When large quantities of a GPCR are needed, for example for the production of antibodies, vectors which direct high level expression of a GPCR may be used. For example, vectors containing the strong, inducible SP6 or T7 bacteriophage promoter may be used.

Yeast expression systems may be used for production of a GPCR. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation.

For the expression of heterologous proteins in insect cell lines is, for example, derivatives of the Lepidopteran baculovirus, *Autographa californica* multicapsid nucleo-virus (AcMNPV) can be used. In this system, foreign gene expression is directed by a very strong late viral promoter, either the polyhedrin or p10 promoters, and a wide array of vectors is available that optimises expression and recovery of recombinant proteins. These vectors enable expression of both membrane-bound and secreted proteins at high levels, and also many post-translational modifications known to occur in mammalian systems, including N- and O-linked glycosylation, phosphorylation, acylation, proteolysis and secreted vaccine components. A number of vectors are commercially available, for example the InsectSelect™ System from Invitrogen.

Expression Systems:

In order to express cDNAs encoding the desired proteins (GPCR and G-protein), one typically subclones the appropriate cDNA into an expression vector that contains a strong promoter to direct transcription, a transcription/translation terminator, and a ribosome-binding site for translational initiation. Suitable bacterial promoters are well known in the art, for example, *E. coli, Bacillus* sp., and *Salmonella*, and kits for such expression systems are commercially available. Similarly, eukaryotic expression systems for mammalian cells, yeast, and insect cells are commercially available. The eukaryotic expression vector may be, for example, an adenoviral vector, an adeno-associated vector, or a retroviral vector.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein and signals required for efficient polyadenylation of the transcript, ribosome binding sites, and translation termination. The nucleic acid sequence encoding the protein may typically be linked to a membrane-targeting signal such as the N-terminal 45 amino acids of the rat Somatostatin-3 receptor sequence to promote efficient cell-surface expression of the recombinant protein, which is useful for cell-surface receptors. Additional elements may include, for example, enhancers.

An expression cassette should also contain a transcription termination region downstream of the structural gene to provide for efficient termination. The termination region may be obtained from the same gene as the promoter sequence or may be obtained from different genes.

For expression of the proteins, conventional vectors for expression in eucaryotic or procaryotic cells well known in the art may be used. Examples of vectors include bacterial expression vectors, for example plasmids including pBR322-based plasmids, pSKF, and pET23D, and fusion expression systems, for example GST and LacZ.

Expression vectors containing regulatory elements from eukaryotic viruses are typically used in eukaryotic expression vectors, for example SV40 vectors, cytomegalovirus vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, pcDNA3.1, pIRES and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase.

The elements that are typically included in expression vectors also include a replicon that functions in *E. coli*, a gene encoding drug resistance to permit selection of bacteria that harbor recombinant plasmids, and unique restriction sites in non-essential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

In bacterial systems the GPCR cDNA fragment may be expressed alone or as a fusion protein wherein the GPCR of interest is fused to the *E. coli* periplasmic maltose-binding protein (MBP) wherein the MBP, including its signal peptide, is linked to the amino terminus of the GPCR. The wild-type GPCR cDNA or the MBP:GPCR fusion cDNA is subcloned into a suitable plasmid, for example pBR322, where in *E. coli*, GPCR expression is driven by the lac wild-type promoter. Methods of expression of GPCRs in *E. coli* are described, for example, in "G-protein coupled receptors (Signal Transduction Series)"; Editors: Tatsuya Haga and Gabriel Berstein, 1st ed., pp. 265-280 CRC Press—Boca Raton Fla.; September 1999.

Genetically engineered yeast systems and insect cell systems which lack endogenous GPCRs provide the advantage of a null background for T1R2 activation screening.

Genetically engineered yeast systems substitute a human GPCR and $G_\alpha$ protein for the corresponding components of the endogenous yeast pheromone receptor pathway. Downstream signaling pathways are also modified so that the normal yeast response to the signal is converted to positive growth on selective media or to reporter gene expression (described by Broach, J. R. and J. Thorner (1996) Nature 384 (supp.):14-16).

Genetically engineered insect systems incorporate a human GPCR and $G_\alpha$ protein that enables receptor coupling the phospholipase C signaling pathway (see for example Knight and Grigliatti, (2004) J Receptors and Signal Transduction 24: 241-256).

Amphibian cell systems, in particular melanophore cells, are described, for example, in WO 92/01810 that describes a GPCR expression system.

Overexpression of T1R2

T1R2 can be overexpressed by placing it under the control of a strong constitutive promoter, for example the CMV early promoter. Alternatively, certain mutations of conserved GPCR amino acids or amino acid domains can be introduced to render the employed GPCR constitutively active.

Transfection of T1R2 Expression Vector Constructs into Cells

Standard transfection methods can be used to produce bacterial, mammalian, yeast or insect cell lines that express large quantities of the protein.

Any known method for introducing nucleotide sequences into host cells may be used. It is only necessary that the particular genetic engineering procedure used be capable of successfully introducing the relevant genes into the host cell capable of expressing the proteins of interest. These methods may involve introducing cloned genomic DNA, cDNA, synthetic DNA or other foreign genetic material into a host cell and include the use of calcium phosphate transfection, polybrene, protoplast fusion, electroporation, liposomes, microinjection, plasma vectors, viral vectors.

For example, the T-Rex™ expression system (Invitrogen Corp., Carlsbad, Calif.) may be used. The T-Rex™ System is a tetracycline-regulated mammalian expression system that uses regulatory elements from the *E. coli* Tn10-encoded tetracycline (Tet) resistance operon. Tetracycline regulation in the T-Rex™ System is based on the binding of tetracycline to the Tet repressor and derepression of the promoter controlling expression of the gene of interest.

Cell Culture

After transfection, the transfected cells may be cultured using standard culturing conditions well known in the art. It will be apparent to the skilled person that different cells require different culture conditions including appropriate temperature and cell culture media.

Modulators that May be Identified by the Assays:

Modulators (ligands, agonists, partial agonists, antagonists, inverse agonists, inhibitors, enhancers) of T1R2 receptor activity can be identified as described herein below. There now follows a definition of the agents which may be identified by said assays.

A modulator is an agent that effects an increase or decrease of one or more of the following: the cell surface expression of a receptor, the binding of a ligand to a receptor, the intracellular response initiated by an active form of the receptor (either in the presence or absence or an agonist). The modulator can itself be an agonist that binds to the receptor, activates it, and thereby modulates an increase in the cellular response.

Modulators include various types of compounds, including small molecules, peptides, proteins, nucleic acids, antibodies or fragments thereof. These can be derived from various sources including synthetic or natural, extracts of natural material, for example from animal, mammalian, insect, plant, bacterial or fungal cell material or cultured cells, or conditioned medium of such cells.

A ligand is an agent that binds to the receptor; it may be an agonist, partial agonist, enhancer, antagonist, or inverse agonist.

An agonist (sweet tastant) is a ligand of the T1R2 receptor that activates the receptor and increases an intracellular response when it binds to a receptor as compared to the intracellular response in the absence of the agonist. Additionally or alternatively, an agonist may decrease internalization of a cell surface receptor such that the cell surface expression of a receptor is increased as compared to the number of cell surface receptors present on the surface of a cell in the absence of an agonist.

A partial agonist is an agonist that only partially activates the receptor in comparison to other agonists that maximally activate the receptor.

An antagonist is a ligand which binds to the receptor at the same (competitive antagonist) or at a different site (allosteric antagonist) as an agonist, but does not activate an intracellular response initiated by an active form of a receptor, thereby inhibiting the intracellular response induced by an agonist as compared to the intracellular response in the presence of an agonist and in the absence of an antagonist.

An inverse agonist, binding to a receptor, decreases the constitutive intracellular response mediated by a receptor as compared to the intracellular response in the absence of the inverse agonist.

An inhibitor decreases the binding of an agonist to the receptor as compared to the binding of the agonist in the absence of inhibitor, and/or decreases the intracellular response induced by an agonist.

An enhancer increases the binding of an agonist to the receptor as compared to the binding of the agonist in the absence of enhancer, and/or increases the intracellular response induced by an agonist.

The activity, or changes in activity, of a receptor binding a ligand and transmitting the signal through, for example, a G-protein (i.e. due to different interactions with modulators) can be determined by the assays described herein-below.

Assays to Identify Modulators of the T1R2 Receptor:

Modulators can be identified using a variety of in vitro and in vivo assays to determine and compare functional effects/parameters. The effects of the test agents upon the function of the receptors can be measured by examining a suitable functional parameters. Any physiological change that affects receptor activity can be used to identify modulators.

Such functional assays are well-known in the art, for example assays using intact cells or tissues isolated from animals based on measuring the concentration or activity or their change of a secondary messenger (including, for example, intracellular calcium ($Ca^{2+}$), cAMP, cGMP, inositol phospate ($IP_3$), diacylglycerol/DAG, arachinoid acid, MAP kinase or tyrosine kinase), ion flux, phosphorylation levels, transcription levels, neurotransmitter levels, and assays based on GTP-binding, GTPase, adenylate cyclase, phospholipid-breakdown, diacylglycerol, inositol triphosphate, arachidonic acid release, PKC, kinase and transcriptional reporters. Some suitable assays are, for example, described in WO 01 18050.

Receptor activation typically initiates subsequent intracellular events, for example, increases in second messengers, for example $IP_3$, which releases intracellular stores of calcium ions. Activation of some G-protein coupled receptors stimulates the formation of inositol triphosphate (IP3) through phospholipase C-mediated hydrolysis of phosphatidylinositol. $IP_3$ in turn stimulates the release of intracellular calcium ion stores. Thus, a change in cytoplasmic calcium ion levels, or a change in second messenger levels such as $IP_3$ can be used to determine G-protein coupled receptor activity.

All functional assays may be performed by samples containing cells expressing the receptor on their surfaces or on isolated cell membrane fractions. Useful cells are described herein-above. Instead of samples with separate cells or cell membranes, tissues from transgenic animals may be used.

To identify a modulator which is not an agonist itself (e.g. an antagonist, partial agonist, inverse agonist, inhibitor, or enhancer), samples with and without test agent are compared. For examples, a control (with agonist but without modulator) is assigned a relative receptor activity value of 100. A decrease in activity relative to the control identifies an inhibitor, antagonist or inverse agonist, an increase identifies an enhancer. Usually, an increase or decrease in the measured activity of 10% or more in a sample with test agent compared to a sample without test agent or compared to a sample with test agent but based on cells that do not express T1R2 (mock-transfected cells) can be considered significant.

Identification of Agonists or Partial Agonists:

To identify an agonist or partial agonist, a sample with test agent is compared to a positive control with an agonist (for example perillartine), or alternatively/additionally, samples with and without test agent are compared in their receptor activity. For example, an agonist or partial agonist will have a biological activity corresponding to at least 10% of the maximal biological activity of the positive control sweet tastant when the agonist or partial agonist is present at 100 mM or less, for example it may have a maximal biological activity comparable to the agonist or higher. Maximal biological activity is defined as the maximal achievable receptor response to an agonist, for example perillartine, that can be achieved within a given receptor assay format and this response fails to increase further despite application of increasing concentrations of that same agonist.

Alternatively, an increase in the measured activity of, for example, 10% or more in a sample with test agent is compared to a sample without test agent or is compared to a sample with test agent but based on cells that do not express T1R2 (mock-transfected cells).

To identify antagonists, receptor activity in the presence of a known agonist with and without a test agent is compared. Antagonists show a reduction of agonist-stimulated receptor activity, for example by at least 10%.

To identify inverse agonists, receptor activity in the presence of a known agonist with and without a test agent is compared in samples comprising animals/cells/membranes that overexpress the receptor as described herein-above. Inverse agonists show a reduction of constitutive activity of the receptor, for example by at least 10%.

Various examples of suitable detection methods that measure T1R2 homomeric receptor activity in assays described herein-above follow.

Detection of Changes of Cytoplasmatic Ions or Membrane Voltage:

Cells are loaded with ion sensitive dyes to report receptor activity, as described in detail in "G-protein coupled receptors (Signal Transduction Series)", CRC Press 1999; 1$^{st}$ Edition; Eds Haga and Berstein. Changes in the concentration of ions in the cytoplasm or membrane voltage are measured using an ion sensitive or membrane voltage fluorescent indicator, respectively.

Calcium Flux:

Intracellular calcium release induced by the activation of GPCRs is detected using cell-permeant dyes that bind to calcium. The calcium-bound dyes generate a fluorescence signal that is proportional to the rise in intracellular calcium. The methods allow for rapid and quantitative measurement of receptor activity.

Cells used are transfected cells that co-express the T1R2GPCR and a G-protein which allows for coupling to the phospholipase C pathway as described herein-above. Negative controls include cells or their membranes not expressing T1R2 (mock transfected), to exclude possible non-specific effects of the candidate compound.

The calcium flux detection protocol is described in detail in "G-protein coupled receptors (Signal Transduction Series)"; Editors: Tatsuya Haga and Gabriel Berstein, 1st ed., 424 pp. CRC Press—Boca Raton Fla.; September 1999, and an adapted version with is summarised below:

Day 0: 96-well plates are seeded with 8.5K cells per well and maintained at 37° C. overnight in nutritive growth media.

Day 1: Cells are transfected using 150 ng of GPCR DNA and 0.3 μl of Lipofectamine 2000 (Invitrogen) per well. Transfected cells are maintained at 37° C. overnight in nutritive growth media.

Day 2: Growth media is discarded and cells are incubated for 1 hour (at room temperature in the dark) with 75 μl of calcium assay solution consisting of 1.5 μM Fluo-4 AM (Molecular Probes) and 2.5 μM probenicid dissolved in a Hanks balanced salts solution (HBSS) that has been supplemented with 10 mM Hepes, 200 μM calcium chloride and 0.1% bovine serum albumin, pH 7.4 at 37° C.

125 μl of wash buffer consisting of 2.5 mM probenicid dissolved in a Hanks balanced salts solution (HBSS) that has been supplemented with 10 mM Hepes, 200 μM calcium chloride and 0.1% bovine serum albumin, pH 7.4 at 37° C., is added to each well and the plate is further incubated for 30 minutes at room temperature in the dark.

Buffer solutions are discarded and plate is washed 3 times with 100 μl wash buffer and cells are reconstituted in 200 μl of wash buffer and incubated for 15 minutes at 37° C.

The plate is placed in a fluorescent microplate reader, for example the Flexstation (Molecular Devices) or the FLIPR (Molecular Devices) and receptor activation is initiated following addition of 20 μl of a 10× concentrated ligand stock solution. Fluorescence is continuously monitored for 15 seconds prior to ligand addition and for 45-110 seconds after ligand addition. Receptor activation levels are defined as by the two following equations: % Activation=(Maximum fluorescence−baseline fluorescence/baseline fluorescence)*100 or Fluorescence Increase=Maximum Fluorescence−baseline fluorescence, where baseline fluorescence represents the average fluorescence levels prior to ligand addition.

Useful cells are mammalian cells as described herein-above, for example HEK293T cells and HEK293 T-Rex™ cells. Cells may be transfected with a GPCR and a G-Protein transiently or stably as is well known in the art. An excellent heterologous expression system is described in detail in WO 2004/055048.

A calcium flux assay can be performed, for example, as described in example 1 herein-below.

The identification of a modulator is performed as described above subject to the following modifications. The signals are compared to the baseline level of T1R2 activity obtained from recombinant cells expressing T1R2 in the presence of an agonist but in the absence of a test agent. An increase or decrease in T1R2 activity, for example of at least 2 fold, at least 5 fold, at least 10 fold, at least a 100 fold, or more identifies a modulator.

Alternatively, the identification involves an increase or decrease fluorescence intensity of, for example, 10% or more, when compared to a sample without modulator, or when compared to a sample with modulator but in cells that do not express the T1R2 polypeptide (mock-transfected cells).

Adenylate Cyclase Activity:

Assays for adenylate cyclase activity are performed, for example, as described in detail by Kenimer & Nirenberg, 1981, Mol. Pharmacol. 20: 585-591. Reaction mixtures are incubated usually at 37° C. for less than 10 minutes. Following incubation, reaction mixtures are deproteinized by the addition of 0.9 ml of cold 6% trichloroacetic acid. Tubes are centrifuged and each supernatant solution is added to a Dowex AG50W-X4 column. The cAMP fraction from the column is eluted with 4 ml of 0.1 mM imidazole-HCl (pH 7.5) into a counting vial in order to measure the levels of cAMP generated following receptor activation by the agonist. Control reactions should also be performed using protein homogenate from cells that do not express a T1R2 polypeptide.

IP3/Ca$^{2+}$ Signals

In cells expressing G-proteins, signals corresponding to inositol triphosphate (IP3)/Ca$^{2+}$ and thereby receptor activity can be detected using fluorescence. Cells expressing a GPCR may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EDTA, to distinguish fluorescence response resulting from calcium release from internal stores.

Phospholipase C/Intracellular Ca$^{2+}$ Signals

T1R2 is expressed in a cell with a G-protein that links the receptor to a phospholipase C signal transduction pathway. Changes in intracellular Ca$^{2+}$ concentration are measured, for example using fluorescent Ca$^{2+}$ indicator dyes and/or fluorometric imaging.

GTPase/GTP Binding:

For a GPCR including T1R2, a measure of receptor activity is the binding of GTP by cell membranes containing the GPCR. Measured is the G-protein coupling to membranes by detecting the binding of labelled GTP.

Membranes isolated from cells expressing the receptor are incubated in a buffer containing 35S-GTPγS and unlabelled GDP. Active GTPase releases the label as inorganic phosphate, which is detected by separation of free inorganic phosphate in a 5% suspension of activated charcoal in 20 mM H$_3$PO$_4$, followed by scintillation counting. The mixture is incubated and unbound labelled GTP is removed by filtration onto GF/B filters. Bound and labelled GTP is measured by liquid scintillation counting. Controls include assays using membranes isolated from cells not expressing T1R2 (mock-transfected), in order to exclude possible non-specific effects of the test agent. The method is described in detail by Traynor and Nahorski, 1995, Mol. Pharmacol. 47: 848-854.

To identify modulators, as described herein-above, a change (increase or decrease) of 10% or more in GTP binding or GTPase activity is usually sufficient. However, to identify agonists, the assays described herein-above are performed subject to the following modifications. An agent is identified as an agonist usually if the activity is at least 50% of that of a known agonist (perillartine) when the compound is present at 100 mM or less, for example 10 to 500 µM, for example about 100 µM, or if it will induce a level the same as or higher than that induced by a known agonist.

Microphysiometer or Biosensor

Such assays can be performed as described in detail in Hafner, 2000, Biosens. Bioelectron. 15: 149-158.

Arachinoid Acid

The intracellular level of arachinoid acid is employed as an indicator of receptor activity. Such a method is described in detail by Gijon et al., 2000, J. Biol. Chem., 275:20146-20156.

cAMP/cGMP:

Intracellular or extracellular cAMP is measured using a cAMP radioimmunoassay (RIA) or cAMP binding protein, for example as described by Horton & Baxendale, 1995, Methods Mol. Biol. 41: 91-105. Alternatively, a number of kits for the measurement of cAMP are commercially available, for example the High Efficiency Fluorescence Polarization-based homogeneous assay by LJL Biosystems and NEN Life Science Products. Alternatively, the intracellular or extracellular levels of cGMP may measured using an immunoassay. For example, the method described in Felley-Bosco et al., Am. J. Resp. Cell and Mol. Biol., 11:159-164 (1994), may be used to determine the level of cGMP. Alternatively an assay kit for measuring cAMP and/or cGMP as described in U.S. Pat. No. 4,115,538 can be used.

Negative controls with mock-transfected cells or extracts thereof to exclude possible non-specific effects of test agents should be used.

DAG/IP3:

Second messengers Diacylglycerol (DAG) and/or inositol triphosphate (IP3), which are released by Phospholipid breakdown, that is caused by receptor activity, can be detected and used as an indicator of T1R2 activity, for example as described in Phospholipid Signalling Protocols, edited by Ian M. Bird, Totowa, N.J., Humana Press, 1998. Alternatively, kits for the measurement of inositol triphosphates are available commercially from Perkin Elmer and CisBio International.

Negative controls with mock-transfected cells or extracts thereof to exclude possible non-specific effects of test agents should be used.

PKC Activity:

Growth factor receptor tyrosine kinases can signal via a pathway involving activation of Protein Kinase C (PKC), which is a family of phospholipid- and calcium-activated protein kinases.

Increases in gene products induced by PKC show PKC activation and thereby receptor activity. These gene products include, for example, proto-oncogene transcription factor-encoding genes (including c-fos, c-myc and c-jun), proteases, protease inhibitors (including collagenase type I and plasminogen activator inhibitor), and adhesion molecules (including intracellular adhesion molecule I (ICAM I)).

PKC activity may be directly measured as described by Kikkawa et al., 1982, J. Biol. Chem. 257: 13341, where the phosphorylation of a PKC substrate peptide, which is subsequently separated by binding to phosphocellulose paper, is measured. It can be used to measure activity of purified kinase, or in crude cellular extracts. Protein kinase C sample can be diluted in 20 mM HEPES/2 mM DTT immediately prior to the assay. An alternative assay can be performed using the Protein Kinase C Assay Kit commercially available by PanVera.

The above-described PKC assays are performed on extracts from cells expressing T1R2.

Alternatively, activity can be measured through the use of reporter gene constructs driven by the control sequences of genes activated by PKC activation.

Negative controls with mock-transfected cells or extracts thereof to exclude possible non-specific effects of test agents should be used.

MAP Kinase Activity:

MAP kinase activity can be measured using commercially available kits, for example, the p38 MAP Kinase assay kit by New England Biolabs, or the FlashPlate™ MAP Kinase assays by Perkin-Elmer Life Sciences. p42/44 MAP kinases or ERK1/2 can be measured to show T1R2 activity when cells with Gq and Gi coupled GPCRs are used, and an ERK1/2 assay kit is commercially available by TGR Biosciences, which measures the phosphorylation of endogenous ERK1/2 kinases following GPCR activation.

Alternatively, direct measurements of tyrosine kinase activity through known synthetic or natural tyrosine kinase substrates and labelled phosphate are well known; the activity of other types of kinases (for example, Serine/Threonine kinases) can be measured similarly.

All kinase assays can be performed with both purified kinases and crude extracts prepared from cells expressing a T1R2 polypeptide.

The substrates of kinases that are used can be either full-length protein or synthetic peptides representing the substrate. Pinna & Ruzzene (1996, Biochem. Biophys. Acta 1314: 191-225) lists a number of phosphorylation substrate sites useful for detecting kinase activities. A number of kinase substrate peptides are commercially available. One that is particularly useful is the "Src-related peptide," (commercially available from Sigma), which is a substrate for many receptor and nonreceptor tyrosine kinases. Some methods require the binding of peptide substrates to filters, then the peptide substrates should have a net positive charge to facilitate binding. Generally, peptide substrates should have at least 2 basic residues and a free-amino terminus. Reactions generally use a peptide concentration of 0.7-1.5 mM.

Negative controls with mock-transfected cells or extracts thereof to exclude possible non-specific effects of test agents should be used.

Transcriptional Reporters/T1R2-Responsive Promoter/Reporter Gene

To identify modulators with reporter gene assays, an at least 2-fold increase or 10% decrease in the signal is significant. An agonist stimulates for example at least 2-fold, 5-fold, 10-fold or more when comparing activity in presence and absence of the test agent.

The intracellular signal initiated by binding of an agonist to T1R2 sets in motion a cascade of intracellular events, the ultimate consequence of which is a rapid and detectable change in the transcription or translation of one or more genes.

The activity of the receptor can therefore be determined by measuring the expression of a reporter gene driven by a promoter responsive to T1R2 activation.

A "promoter" as used herein is one or more transcriptional control elements or sequences necessary for receptor-mediated regulation of gene expression, including one or more of basal promoter, enhancers and transcription-factor binding sites necessary for receptor-regulated expression. Promoters responsive to the intracellular signals resulting from agonist binding to T1R2 are selected and operatively linked to a corresponding promoter-controlled reporter gene whose transcription, translation or ultimate activity is readily detectable and measurable.

Reporter genes may be selected, for example, from luciferase, CAT, GFP, β-lactamase, β-galactosidase, and the so-called "immediate early" genes, c-fos proto-oncogene, transcription factor CREB, vasoactive intestinal peptide (VIP) gene, the somatostatin gene, the proenkephalin gene, the phosphoenolpyruvate carboxy-kinase (PEPCK) gene, genes responsive to NF-kB, and AP-1-responsive genes (including the genes for Fos and Jun, Fos-related antigens (Fra) 1 and 2, IkBα, ornithine decarboxylase, and annexins I and II).

Promoters will be selected according to the selected reporter gene, as will be apparent to the skilled person.

Luciferase, CAT, GFP, β-lactamase, β-galactosidase and assays for the detection of their products are well known in the art. Examples of further reporter genes are described herein-below.

The "immediate early" genes are particularly well suited and are rapidly induced (for example within minutes of contact between the receptor and the effector protein or ligand). Desirable properties in reporter genes include one or more of the following: rapid responsiveness to ligand binding, low or undetectable expression in quiescent cells; induction that is transient and independent of new protein synthesis; subsequent shut-off of transcription requires new protein synthesis; and mRNAs transcribed from these genes which have a short half-life of several minutes to a few hours. Similarly, the promoter may have one, several or all of these properties.

The c-fos proto-oncogene is an example of a gene that is responsive to a number of different stimuli and has an rapid induction. The c-fos regulatory elements include a TATA box that is required for transcription initiation; two upstream elements for basal transcription, and an enhancer, which includes an element with dyad symmetry and which is required for induction by TPA, serum, EGF, and PMA. The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is responsive to levels of intracellular cAMP. Therefore, the activation of a receptor that signals via modulation of cAMP levels can be determined by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other suitable reporter genes and their promoters include the vasoactive intestinal peptide (VIP) gene and its promoter which is cAMP responsive; the somatostatin gene and its promoter which is cAMP responsive; the proenkephalin and its promoter which is responsive to cAMP, nicotinic agonists, and phorbol esters; and the phosphoenolpyruvate carboxy-kinase (PEPCK) gene and its promoter which is cAMP responsive.

Additional examples of reporter genes and their promoters that are responsive to changes in GPCR activity include the AP-1 transcription factor and NF-kB.

The AP-1 promoter is characterised by a consensus AP-1 binding site which is the palindrome TGA(C/G)TCA. The AP-1 site is also responsible for mediating induction by tumor promoters including the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include the genes for Fos and Jun (which proteins themselves make up AP-1 activity), Fos-related antigens (Fra) 1 and 2, IkBα, ornithine decarboxylase, and annexins I and II.

A large number of genes have been identified as NF-KB responsive, and their control elements can be linked to a reporter gene to monitor GPCR activity. Genes responsive to NF-KB include for example those encoding IL-1~, TNF-α, CCR, P-selection, Fas ligand, GM-CSF and IKBa. Vectors encoding NF-KB-responsive reporters are known in the art or can be readily formed using ordinary skill in the art, for example, synthetic NFKB elements and a minimal promoter, or using the NF-KB-responsive sequences of a gene known to be subject to NF-KB regulation. Further. NF-KB responsive reporter constructs are commercially available from, for example, CLONTECH.

A given promoter construct can easily be tested by exposing T1R2-expressing cells, transfected with the construct, to an agonist (for example perillartine). An increase of at least 2-fold in the expression of reporter gene in response to the agonist indicates that the reporter is suitable to measure T1R2 activity.

Controls for transcription assays include both cells not expressing T1R2 but carrying the reporter construct, and cells with a promoterless reporter construct.

Agents that modulate T1R2 activity as shown by reporter gene activation can be verified by using other promoters and/or other receptors to verify T1R2 specificity of the signal and determine the spectrum of their activity, thereby excluding any non-specific signals, for example non-specific signals via the reporter gene pathway.

Inositol Phosphates (IP) Measurement:

Phosphatidyl inositol (PI) hydrolysis can be determined as described in U.S. Pat. No. 5,436,128, which involves labelling of cells with 3H-myoinositol for at least 48 hours or more. The labelled cells are contacted with a test agent for one hour, then these cells are lysed and extracted in chloroform-methanol-water. This is followed by separating the inositol phosphates by ion exchange chromatography and quantifying them by scintillation counting. For agonists, fold stimulation is determined by calculating the ratio of counts per minute (cpm) in the presence of tested agent, to cpm in the presence of buffer control. Likewise, for inhibitors, antagonists and inverse agonists, fold inhibition is determined by calculating the ratio of cpm in the presence of test agent, to cpm in the presence of buffer control (which may or may not contain an agonist).

T1R2 Receptor and Substantially Homologous Polypeptides and Nucleic Acids:

The T1R2 homomeric receptor useful in the methods may be the wildtype receptor, or alternatively a receptor (or nucleotide sequence to form the T1R2 receptor) which is substantially homologous and remains functional (i.e. binds to ligands and is activated by ligands). Such homologous receptors may be, for example, an allelic variant of a human receptor, or a receptor of a different species including rat (about 70% amino acid sequence identity), mouse (about 69% amino acid sequence identity and about 64% nucleic acid identity), or dog (about 76% amino acid sequence identity), or any other species having sufficient amino acid sequence identity to the human receptor.

Further, substantially homologous T1R2 nucleotide or polypeptide sequences may be formed by conservative mutations and/or point mutations and include any conservatively modified variant as detailed below.

With respect to nucleic acid sequences, conservatively modified variants means nucleic acids which encode identical or essentially identical amino acid sequences (conservatively substituted amino acids, i.e. lysine switched to arginine and further examples as explained herein-below).

Because of the degeneracy of the genetic code, a large number of nucleic acids different in sequence but functionally identical encode any given polypeptide/protein. Such nucleic acid variations are "silent variations," which are one species of conservatively modified variations. Each nucleic acid sequence which encodes a polypeptide also describes every possible silent variation of the nucleic acid. Therefore, each codon in a nucleic acid (except AUG, which is ordinarily the only codon for methionine, and TGG, which is ordinarily the only codon for tryptophan) can be modified to yield a functionally identical nucleic acid sequence that will produce an identical polypeptide. Accordingly, each silent variation of a nucleic acid which encodes a polypeptide is implicit in each given nucleic acid sequence.

With respect to amino acid sequences, amino acid substitutions may be introduced using known protocols of recombinant gene technology including PCR, gene cloning, site-directed mutagenesis of cDNA, transfection of host cells, and in-vitro transcription which may be used to introduce such changes to the T1R2 sequence. The variants can then be screened for taste-cell-specific GPCR functional activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gin; ile/leu or val; leu/ile or val; lys/arg or gin or glu; met/leu or tyr or ile; phe/met or leu or tyr; ser/thr; thr/ser; trp/tyr; tyr/trp or phe; val/ile or leu.

An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (1); 5) Isoleucine (I), Leucine (L), Methionine (M), Valine (V); and 6) Phenylalanine (F), Tyrosine (Y), Tryptophan (W).

Another alternative guideline is to allow for all charged amino acids as conservative substitutions for each other whether they are positive or negative.

In addition, individual substitutions, deletions or additions that alter, add or delete a single amino acid or a small percentage (for example up to 31%, or up to 20%, or up to 10%) of amino acids in an encoded sequence are also considered to be conservatively modified variations.

Substantially homologous nucleotide or polypeptide sequences have the degree of sequence identity or hybridize under certain stringent hybridization conditions as indicated below.

% Sequence Identity:

A substantially homologous nucleotide sequence has a % sequence identity of at least 64%, at least 70%, at least 75%, at least 85%, at least 90%, at least 95%, or at least 98%.

A substantially homologous polypeptide sequence has a % sequence identity of at least 69%, at least 75%, at least 80%, at least 85%, at least 90%, at least 95% or at least 98%.

Calculation of % Sequence Identity is determined as follows.

BLAST (Basic Local Alignment Search Tool) is the heuristic search algorithm employed by the programs blastn which is available at the interne website of the National Center For Biotechnology Information.

To determine % identity of a nucleotide query sequence against another nucleotide sequence, Blastn is used, using default parameters of BLAST version 2.2.1.3, including an EXPECT (statistical significance threshold for reporting matches against database sequences) of 10, and DUST filtering.

Stringent Hybridization Conditions:

Nucleotide sequences are considered substantially homologous provided that they are capable of selectively hybridizing to the nucleotide sequences presented herein, or to their complement, under stringent hybridization conditions detailed below. Stringent conditions are temperature of 42° C. in a solution consisting of 50% formamide, 5×SSC, and 1% SDS and washing at 65° C. in a solution consisting of 0.2× SSC and 0.1% SDS (1×SSC=0.15 M NaCl, 0.015 M Na3 Citrate pH 7.0).

Background hybridization may occur because of other nucleotide sequences present, for example, in the cDNA or genomic DNA library being screened.

A positive signal that is at least 2 times the signal strength of the background, optionally 10 times the signal strength of the background hybridization, is considered a specific interaction with (i.e. selective hybridization to) the target DNA. Optionally, a signal that is less than 10 fold as intense as the specific interaction observed with the target DNA is considered background.

The intensity of interaction may be measured, for example, by radiolabelling the probe, for example, with 32P.

Kit to Identify a Modulator:

A kit, for example a screening kit or high throughput screening kit, that comprises recombinant cells that express the T1R2 homomer, or a substantially homologous sequence thereto, but that do not express T1R3; and that comprises an agonist of the T1R2 homomer, for example perillartine is also provided.

Optionally, the cells further comprise a G-protein, for example, for calcium signalling. Suitable G-Proteins are known and described herein-above; the skilled person is aware how to introduce them to the cells if necessary. A very useful chimeric G-Protein is G alpha 16-gustducin 44.

The agonist is provided in suitable concentrations, for example, 1 nM to 10 mM, or 0.1 microM to 1 milliM, for example 0.1 microM to 100 microM.

Optional kit components include, without limitation, a suitable medium for culturing the recombinant cells provided, and a solid support to grow the cells on, for example a cell culture dish or microtiter plate, these optional components will be readily available to the skilled person.

The kit may be used as follows:

(i) The recombinant cells are grown on a solid support.
(ii) Test agents at concentrations from about 1 nM to 100 mM or more are added to the culture medium of defined plates or wells in the presence of the agonist in a suitable concentration.
(iii) A change in a functional response of the cells is determined by comparing the response in presence and absence of the test agent, and the test agent is thereby identified as a modulator.

For example, step (iii) may be performed according to any one of the assays described-herein above, in combination with any one of the detection methods that report receptor activity described herein-above. This may require specifically chosen or adapted recombinant cells, which are also described herein-above.

A suitable assay is, for example, the calcium flux assay to determine activation of T1R2 and its change in response to a test agent.

Confirmation of Identified Modulators

A modulator identified by a method described hereinabove may easily be confirmed by simple sensory experiments using a panel of flavorists or test persons to taste the identified modulators. The compounds are tasted e.g. in water to confirm sweet taste or together with sweet tastants in comparison to a negative control without modulator to confirm a modulator that enhances the sweet taste.

Large Scale Screening Assays

Transcriptional reporter assays and most cell-based assays described herein-above are well suited for screening libraries for agents that modulate T1R2 activity.

The assays may be designed to screen large chemical libraries by automating the assay steps and providing compounds from any convenient source to the assays, which are typically run in parallel (for example in microtiter formats on microtiter plates in robotic assays).

Assays may be run in high throughput screening methods that involve providing a combinatorial chemical or peptide library containing a large number of potential modulators. Such libraries are then screened in one or more assays described herein-above to identify those library agents (particular chemical species or subclasses) that display the activity described herein-above. The modulators thus identified can be directly used or may serve as leads to identify further modulators by making and testing derivatives.

Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.).

Libraries of Test Agents:

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

A rare chemical library is available from Aldrich (Milwaukee, Wis.).

Libraries of natural compounds in the form of bacterial, fungal, plant and animal extracts are commercially available for example from Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Other libraries include protein/expression libraries, cDNA libraries from natural sources, including, for example, foods, plants, animals, bacteria, libraries expressing randomly or systematically mutated variants of one or more polypeptides, genomic libraries in viral vectors that are used to express the mRNA content of one cell or tissue.

In a high throughput assay, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 modulators. If 1536 well plates are used, then a single plate can easily assay from about 100 to about 1500 different compounds. It is possible to assay several different plates per day; assay screens for up to about 6,000-20,000 different compounds is possible.

Types of Test Agents that May be Tested for their T1R2 Modulating Effect in the Assay Methods:

The test agents can be any agent including small chemical compounds, chemical polymers, biological polymers, peptides, proteins, sugars, carbohydrates, nucleic acids and lipids. An agent can be a synthetic compound, a mixture of compounds, a natural product or natural sample, for example plant extract, culture supernatant, or tissue sample.

As examples of sweet tastant compounds, or compounds that modify sweet taste there may be mentioned Theasaponin E1, Acesulfame K, Alitame, Aspartame, CH 401, Dulcin, Erythritol, Guanidine Sweetener, Isomalt, Isomaltosylfructoside, Isoraffinose, NC 174, Neotame, Perillartine, Phenylacetylglycyl-L-Lysine, Saccharin, SC 45647, sodium Cyclamate, Sorbitol, Sucralose, Sucrononic Acid, Suosan, Superaspartame, Methyl alpha-L-arabinoside, Methyl beta-L-arabinoside, Methyl beta-D-Glucoside, Methyl a-D-mannoside, Methyl beta-L-xylopyranoside, Methyl alpha-D-xyloside, Methyl alpha-D-Glucoside 2,3-Di-threonine, Methyl alpha-D-Glucoside 2,3-Di-isoleucine, Protocatechuic Acid, Cynarin, Glycyphyllin, Rebaudioside C, Abrusoside A, Abrusoside B, Abrusoside C, Abrusoside D, Abrusoside E, Apioglycyrrhizin, Araboglycyrrhizin, Baiyunoside, Brazzein, Bryodulcoside, Carnosifloside V, Carnosifloside VI, D. cumminsii, Cyclocarioside A, Cyclocarioside I, Dulcoside A, Fluorene-4-alpha,6-dicarboxylic acid, 4-beta, 10-alpha-dimethyl-1,2,3,4,5,10-hexahydror-Gaudichaudioside A, Glycyrrhizic Acid, Hernandulcin, Hernandulcin, 4beta-hydroxy-Hesperitin-7-Glucoside Dihydrochalcone, Huangqioside E, Huangqioside E, 3-Hydroxyphloridzin, Kaempferol, 2,3-Dihydro-6-Methoxy 3-O-Acetate, Mabinlin Maltosyl-Alpha-(1,6)-Neohesperidin Dihydrochalcone, Mogroside IIE, Mogroside III, Mogroside IIIE, Mogroside IV, Mogroside V, 11-Oxo Mogroside V, Monatin, Monellin, Monoammonium Glycyrrhizinate (Mag), Mukurozioside lib, Naringin Dihydrochalcone, Neoastilbin, Neohesperidin Dihydrochalcone (NHDHC), Neomogroside, Osladin, Pentadin, Periandrin I, Periandrin II, Periandrin III, Periandrin IV, Periandrin V, Phlomisoside I, Phlorizin, Phyllodulcin, Polypodoside A, Potassium magnesium calcium glycyrrhizin, Pterocaryosides A, Pterocaryosides B, Quercetin, 2,3-Dihydro-3-O-Acetate, Quercetin, 2,3-Dihydro-6-Methoxy-Quercetin, 2,3-Dihydro-6-Methoxy-3-O-Acetate, Rebaudioside A, Rebaudioside B, Rubusoside, Scandenoside R6, Siamenoside I, Sodium glycyrrhizinate, Steviolbioside, Stevioside, Stevioside, alpha-Glycosyl Suavioside A, Suavioside B, Suavioside G, Suavioside H, Suavioside I, Suavioside J, Thaumatin, Triammonium Glycyrrhizinate (TAG), Trilobtain Selligueain A, Haematoxylin, Maltitol, Mannitol, Methyl alpha-D-Glucoside 2,3-Di-aspartic acid, Benzoic Acid, 2-(4-Dimethylaminobenzoyl)-Benzoic Acid, 2-Hydroxy-4-aminomethyl-Benzoic Acid, 2-(3-Hydroxy-4-Methoxybenzoyl)-Methyl beta-D-fructoside, Methyl alpha-D-galactoside, Methyl beta-D-galactoside, Curculin, Strogin 1, Strogin 2, Strogin 4, Miraculin, Phenylacetic Acid, 3,4-Dimethoxy-Aminobenzoic Acid, 3-Anisic Acid, Benzyl alcohol, 3-Amino-4-n-propoxyl, 3,4-Caffeic Acid, Cinnamic Acid, Dihydroxycinnamic Acid, 2,4-Ferulic Acid, Hydrolyzed Guar Gum, Hydroxyaminobenzoic Acid, 2,4-Nigerooligosaccharides, Sugarcane Bagasse Extract, Dihydroxybenzoic Acid, 2,3-Dihydroxybenzoic Acid, 2,4-Coumaric Acid, p-Dihydroxybenzoic Acid, 3,5-Hydroxybenzoic Acid, 3-Gurmarin, Gymnemasaponin III, Gymnemasaponin IV, Gymnemasaponin V, Gymnemic Acid I, Gymnemic Acid II, Gymnemic Acid III, Gymnemic Acid IV, Hodulcin, Jujubasaponin II, Jujubasaponin III, Propionic Acid, (−)-2-(4-Methoxyphenoxy)-Ziziphin, Ethyl Maltol, Maltol, Butanoic Acid, 2-Oxo-3-Methyl-Alanine, N-(1-Methyl-4-oxo-2-imidazolin-2-yl) Creatinine, Abrusoside E, mono-methyl ester, Lactitol, Periandrinic acid I, monoglucuronide, Periandrinic acid II, monoglycuronide, Xylitol, Tagatose, d-Benzoyloxyacetic acid, 4-Methoxy Hoduloside I, 4-Nitrophenyl a-D-galactoside, 4-Nitrophenyl alpha-D-glucoside, 4-Nitrophenyl beta-D-glucoside, 4-Nitrophenyl alpha-D-mannopyranoside, Urea, (N-(4-cyanophenyl)-N'-((sodiosulfo)methyl)-Chloramphenicol, Chlorogenic Acid, Methyl alpha-D-Glucoside, Methyl alpha-D-Glucoside 2,3-Di-alanine, Methyl alpha-D-Glucoside 2,3-Di-glycine, Methyl alpha-D-Glucoside 2,3-Di-proline, Methyl alpha-D-Glucoside 2,3-Di-valine, Aniline, 2-Butoxy-5-Nitro-Aniline, 2-Ethoxy-5-Nitro-Aniline, 2-Methoxy-5-Nitro-Aniline, 3-Nitro-(+)-Baiyunol-beta-D-gluccoside-alpha-D-glucoside, Aniline, 1,3-Hydroxy-4-methoxybenzylAniline, 2-Propxy-5-Nitro-(P4000)Benzo-1,4-dioxane 2-(3-Hydroxy-4-Methoxyphenyl)-Benzoe-1,3-dioxan-4-one 2-(3-Hydroxy-4-methoxyphenyl)-Benzoic Acid, 2-Benzoyl-4-Methoxy-Benzoic Acid, 2-(4-Methoxybenzoyl)-Benzo-1,3 (4H)-xathiane, 2-(3-Hydroxy-4-Methoxyphenyl)-Benzo-1,4-xathiane 3-(3-Hydroxy-4-methoxyphenyl)-Butanoic acid, 4-[3,5-dihydroxy-4-[3-(3-hydroxy-4-methoxyphenyl)-1-oxopropyl]phenoxy]-2-hydroxy-monosodium salt, Butanoic acid, 4-[3,5-dihydroxy-4-[3-(3-hydroxy-4-methoxyphenyl)-1-oxopropyl]phenoxy]-3-oxo-monosodium salt, Cyclohexadiene-1,4,1-Carboxaldehyde-4-(Methoxymethyl)-, (E)oxime Ethylbenzene, beta-(1,3-Hydroxy-4-methoxybenzyl)-Hespertin Dihydrochalcone, 3'-Carboxy-Hespertin Dihydrochalcone, 3'-Formyl-Isocoumarin, 3,4-Dihydro-3-(3-Hydroxy-4-methoxy)-Perillartine, 8,9-epoxy-Phenyl 3-Hydroxy-4-methoxybenzyl Ether, Phosphonic acid, [3-[3,5-dihydroxy-4-[3-(3-hydroxy-4-methoxyphenyl)-1-oxopropyl]phenoxy]propyl]monopotassium salt, Stevioside analogue, Sulfamic acid, [2-[3,5-dihydroxy-4-[3-(3-hydroxy-4-methoxyphenyl)-1-oxopropyl]phenoxy]ethyl]-monopotassium salt, Urea, and N-(4-cyanophenyl)-N'-(2-carboxyethyl)-L-Theanine.

Identified sweet tastants may include, for example, artificial sweeteners that are able to elicit a sweet taste sensation. These are of particular interest as they can be used to replace sugar compounds, for example, to reduce calories or to provide consumables that are more healthy for the teeth. Consumables include food products, beverages, oral care products, and compositions for admixture to such products, in particular flavour compositions. Flavour compositions may be added to processed foods or beverages during their processing, or they may actually be consumables in their own right, e.g. condiments such as sauces and the like. Sweet tastants are particularly interesting in confectionary and other sweet consumables including desserts, but also in savoury and sweet-sour consumables. Non-limiting, examples of consumables include confectionary products, cakes, cereal products, baker's products, bread products, gums, chewing gums, sauces (condiments), soups, processed foods, cooked fruits and vegetable products, meat and meat products, egg products, milk and dairy products, cheese products, butter and butter substitute products, milk substitute products, soy products, edible oils and fat products, medicaments, beverages, alcoholic drinks, beers, soft drinks, food extracts, plant extracts, meat extracts, condiments, sweeteners, nutraceuticals, pharmaceutical and non-pharmaceutical gums, tablets, lozenges, drops, emulsions, elixirs, syrups and other preparations for making beverages, instant beverages and effervescent tablets.

T1R2 Sequences

The sequences are shown in the sequence listing hereinbelow. SEQ ID NO:1 corresponds to the nucleotide/nucleic acid sequence encoding the T1R2 receptor, SEQ ID NO: 2 corresponds to the polypeptide/amino acid sequence of the T1R2 receptor protein.

There now follows a series of examples that serve to illustrate the above-described methods. The following examples are merely illustrative and should not be construed as limiting the methods or kit in any manner.

EXAMPLES

All examples use the human receptors.

Example 1

Fluo-4 Calcium Assay

Fluo-4 is a fluorescent indicator for intracellular calcium and allows to determine changes in the calcium concentration, in particular an increase in response to receptor activation occurring after ligand addition (for example perillartine).

HEK293 cells stably expressing G alpha 16-gustducin 44 and transfected as described in example 2, 3 or 4 were used as host cells.

Black, clear-bottom 96-well plates were used for all assays. They were seeded the day before with 8500 transfected cells per well and maintained at 37° C. overnight in a growth medium appropriate for the cells used. For HEK293 cells, Dulbecco's Modified Eagle medium containing high glucose, L-glutamine, pyroxidine hydrochloride, and supplemented with 10% fetal bovine serum was used for growth and maintenance of the HEK293 cells.

At the time of the assay, the growth medium was discarded and cells were incubated for 1 hour (at 37° C. in the dark) with 50 µL of a calcium assay solution consisting of 1.5 µM Fluo-4 AM (Molecular Probes™, Invitrogen, US) and 2.5 µM probenicid (Sigma-Aldrich) dissolved in a C1 buffer solution. C1 buffer solution contains 130 mM NaCl, 5 mM KCl, 10 mM Hepes, 2 mM CaCl2 and 10 mM glucose (pH 7.4).

After the initial 1 hour loading period, the plates were washed 5 times with 100 µl per well of C1 buffer using an automated plate washer (BioTek) and after washing, the plate was further incubated for 30 minutes at room temperature in the dark to allow for complete de-esterification of the Fluo-4-AM. The buffer solutions were discarded, the plate was washed 5 times with 100 µl C1 wash buffer and finally the cells were reconstituted in 180 µl of C1 wash buffer.

For assay reading, the plate was placed in a FLIPR (fluorescence imaging plate reader (FLIPR-Tetra, Molecular Devices)), and receptor activation was initiated following addition of 20 µl of a 10× concentrated ligand stock solution.

Fluorescence was continuously monitored for 15 seconds prior to ligand addition and for 105 seconds after ligand addition (45-105 sec may be sufficient).

Receptor activation is given in relative fluorescence units (RFU) and is defined by the following equation:

Fluorescence Increase=Maximum Fluorescence−baseline fluorescence, wherein the baseline fluorescence represents the mean fluorescence calculated for the first 10 to 15 seconds prior to ligand addition.

As a negative control, mock transfected cells were exposed to the same concentration of ligand and the concentration of calcium traces not corresponding to a signal was determined.

Cells with an activated receptor were identified by the signal (RFU) being significantly above the negative control.

Example 2

Transfections of T1R2, T1R3, and T1R2/T1R3 and Heterologous Expression

To form a T1R2 vector construct, cDNA fragments containing the entire protein coding sequences for human T1R2 and T1R3 were isolated from a human fungiform cDNA library, fully sequenced and then subcloned into pcDNA3.1 (Invitrogen).

HEK293T cells that stably express G16gust44 (formed as described in WO 2004/055048) were transfected with the T1R2 vector construct as follows:
On day 0, the HEK293T/G16gust44 cells were plated in 96-well plates at a density of 8,500 cells per well and grown overnight in selective growth media.
On day 1, the media was changed to an antibiotic-free and serum-free growth medium and the cells were transfected using 75 ng T1R2 or T1R3 vector construct DNA and 0.3 µl of Lipofectamine 2000 (Invitrogen).

For transfection of the T1R2/T1R3 heterodimer, 75 ng of each T1R vector construct was combined for a total of 150 ng and used in conjunction with 0.3 µl of Lipofectamine 2000. The lipofectamine/DNA mixture was incubated on the cells for 3-4 hours and then replaced with an antibiotic-free, serum-containing growth medium. The cells were grown overnight and the Fluo-4 calcium assay was performed as described in example 1.

The cells transiently transfected with the expression construct were identified using a fluorescence imaging plate reader (FLIPR-Tetra, Molecular Devices) as described in example 1.

Example 3

Activation of T1R2 in the Presence and Absence of T1R3 by Perillartine

The intracellular calcium response following stimulation with 50 µM perillartine was determined in HEK293T cells stably expressing G16gust44 and transfected with the T1R2 monomer, with the T1R3 monomer, and with both T1R2 and T1R3 to give the T1R2/T1R3 dimer.

The transfections were performed according to the methods described in example 2, results were calculated as described in example 1 (data indicates the net increase in fluorescence over baseline after stimulation (RFU); the mean±Standard deviation of six replicates is given).

A significant increase of the calcium signal was observed in cells expressing the T1R2 monomer; the signal was comparable intensity to the signal of the T1R2/T1R3 dimer. No significant increase was observed in cells expressing the T1R3 monomer; their signal was well below of the signal of the negative control (mock transfected cells expressing only the G16gust44 chimeric G-protein).

|  | SIGNAL AVERAGE [RFU] | SIGNAL STD. DEVIATION (+/−) [RFU] |
| --- | --- | --- |
| T1R2 monomer | 944.9 | 205.5 |
| T1R3 monomer | 165.6 | 19.7 |
| T1R2/T1R3 dimer | 1279.6 | 141.9 |
| Negative Control (MOCK TRANSFECTED) | 353.5 | 137.7 |

An experiment with the artificial sweeteners cyclamate, aspartame, D-tryptophan, sucralose, and stevioside showed signals not significantly above the signals observed for the negative controls (mock transfected cells) for the T1R2 monomer, while the T1R2/T1R3 dimer with these artificial sweeteners showed strong signals comparable to the signal intensity of perillartine.

Example 4

Transfection of T1R2 to Form Stable Cell Lines Expressing T1R2

A human T1R2/pcDNA4-Zeocin construct was linearized by digesting 5 ug with Pvu II and then purified using the Wizard DNA Clean-Up System (Promega). The DNA was transfected using the Lipofectamine 2000 reagent into cells that already stably express the G16gust44 G-protein (formed as described in WO 2004/055048).

After 24 hours, the transfected cells were trypsinized and re-plated in 10× dilutions up to 1:100,000 in 150 cm dishes containing selective growth media (DMEM containing 10% FBS, G418 (0.36 mg/mL), and Zeocin (0.2 mg/mL). After 7-14 days, G418/Zeocin-resistant foci were picked, expanded for 1-2 weeks and then functionally analyzed for their response to 50 μM perillartine in the calcium flux assay (described in more detail in example 1). For this calcium flux assay FLIPR is used and clones were plated at a density of 15,000 cells per well in a 96-well black, clear bottom plate, allowed to grow for 40-48 hours before being analyzed. Responses to 50 μM perillartine were compared to signals obtained with a negative control (C1 buffer) in order to confirm and quantify receptor-specific signals.

For results, see table below. The signal average of the experiment is given, as well as the standard deviation (STD) in RFU. Two clones were analysed. Non-transfected cells expressing G16gust44 only serve as a general negative control. A significant increase of the calcium signal was observed in multiple clonal cell lines stably expressing the T1R2 monomer and the perillartine-dependent signals obtained were at least 10-fold greater than those obtained in the negative control cells expressing only the G16gust44 chimeric G-protein.

|  |  | Signal average [RFU] | STD [RFU] |
|---|---|---|---|
| Negative control: G16gust44 ONLY | PERILLARTINE | 368.71 | 160.83 |
|  | C1-Negative control | 77.97 | 8.48 |
| T1R2/G16gust44 CLONE 2 | PERILLARTINE | 4336.25 | 452.84 |
|  | C1-Negative control | 345.69 | 35.33 |
| T1R2/G16gust44 CLONE 4 | PERILLARTINE | 5288.47 | 380.10 |
|  | C1-Negative control | 199.66 | 21.57 |

While the methods and kit have been described above in connection with certain illustrative embodiments, it is to be understood that other similar embodiments may be used or modifications and additions may be made to the described embodiments for performing the same function. Further, all embodiments disclosed are not necessarily in the alternative, as various embodiments may be combined to provide the desired characteristics. Variations can be made by one having ordinary skill in the art without departing from the spirit and scope of the disclosure. Therefore, the method and kit should not be limited to any single embodiment, but rather construed in breadth and scope in accordance with the recitation of the attached claims.

The invention claimed is:

1. A method to identify an agent that modulates sweet taste signaling in taste cells comprising:
   (i) contacting cells that express a homomeric sweet receptor that responds to perillartine with an agent, optionally in presence of another agent;
   (ii) comparing receptor activity to cells that express a homomeric sweet receptor that have been contacted with perillartine but no agent; and
   (iii) determining whether at least one agent affects the functional activity of said homomeric sweet receptor in said cells by at least one functional response in said cells; wherein said homomeric sweet receptor comprises a polypeptide with a sequence at least 90% identical to SEQ ID NO:2.
   and wherein the homomeric sweet receptor expressing cells do not express a T1R3 receptor.

2. The method of claim 1, wherein the cells also express a G-protein.

3. The method of claim 2, wherein the G-protein comprises a chimeric G-protein.

4. The method of claim 3, wherein the chimeric Gaq-Gustducin G-protein comprises the chimeric G-protein G alpha 16-gustducin 44.

5. The method of claim 1, wherein (iii) is performed by measuring a change in or caused by intracellular messengers.

6. The method of claim 2, wherein the functional response is determined by measuring a change in an intracellular messenger selected from IP3 and calcium$^{2+}$.

7. The method of claim 1, wherein the cells are selected from the group consisting of eucaryotic cells, yeast cells, insect cells, mammalian cells, amphibian cells, and worm cells.

8. The method of claim 7, wherein the cells are mammalian cells.

9. The method of claim 8, wherein the cells are mammalian cells selected from the group consisting of CHO, COS, HeLa and HEK-293 cells.

10. The method of claim 1, wherein (i) further comprises contacting the homomeric sweet receptor with a test agent in presence of perillartine.

11. A kit comprising:
(i) recombinant cells that express a homomeric receptor that responds to perillartine, wherein said homomeric sweet receptor comprises a polypeptide with a sequence at least 90% identical to SEQ ID NO:2, and wherein the homomeric sweet receptor expressing cells do not express a T1R3 receptor; and
(ii) perillartine,
for combined use to identify test agents as modulators of the homomeric sweet receptor.

12. A method of using the kit of claim 11 comprising:
(i) growing recombinant cells on a solid support;
(ii) adding test agents to a culture medium of defined plates or wells in the presence of perillartine in a suitable concentration, and
(iii) determining a change in a functional response of the cells by comparing the response in presence and absence of the test agent, and the test agent is thereby identified as a modulator of the homomeric sweet receptor.

13. The method of claim 12, comprising adding a test agent in an amount from about 1 nM to about 100 mM to a culture medium of defined plates or wells in the presence of the agonist in a suitable concentration.

14. A method to identify an agent that modulates sweet taste signaling in taste cells comprising:
(i) contacting cells that express a homomeric sweet receptor that responds to perillartine and which express a chimeric G-protein with an agent, optionally in presence of another agent;
(ii) comparing receptor activity to cells that express a homomeric sweet taste receptor that have been contacted with perillartine but no agent; and
(iii) determining whether at least one agent affects the functional activity of said homomeric sweet receptor in said cells by at least one functional response in said cells; wherein said homomeric sweet receptor comprises a polypeptide with a sequence at least 90% identical to SEQ ID NO:2,
and wherein the homomeric sweet receptor expressing cells do not express a T1R3 receptor.

15. The method of claim 14, wherein the chimeric G-protein comprises a chimeric Gaq-Gustducin G-protein.

16. The method of claim 15, wherein the chimeric Gaq-Gustducin G-protein comprises the chimeric G-protein G alpha 16-gustducin 44.

17. The method of claim 14, wherein (iii) is performed by measuring a change in or caused by intracellular messengers.

18. The method of claim 17, wherein the functional response is determined by measuring a change in an intracellular messenger selected from IP3 and calcium$^{2+}$.

19. The method of claim 14, wherein the cells are selected from the group consisting of eucaryotic cells, yeast cells, insect cells, mammalian cells, amphibian cells, and worm cells.

20. The method of claim 19, wherein the cells are mammalian cells selected from the group consisting of CHO, COS, HeLa and HEK-293 cells.

* * * * *